United States Patent [19]

Gros et al.

[11] Patent Number: 4,897,398

[45] Date of Patent: Jan. 30, 1990

[54] HYDROCHLORIDES OF CHLORIDES OF 2-AMINOALKYL-9-HYDROXY-ELLIPTICINIUM DERIVATIVES AND PHARMACEUTICAL COMPOSITIONS CONTAINING THEM

[75] Inventors: Pierre Gros, Montpellier, France; Emilio Crisafulli, Milan, Italy; Guy Mazue, Mantry, France

[73] Assignees: Sanofi; Centre National de la Recherche Scientifique (C.N.R.S.), both of Paris, France

[21] Appl. No.: 877,801

[22] Filed: Jun. 24, 1986

[30] Foreign Application Priority Data

Jul. 4, 1985 [FR] France .................. 85 10257

[51] Int. Cl.$^4$ ............................. A61K 31/475
[52] U.S. Cl. ............................. 514/284; 546/70
[58] Field of Search .................. 546/70; 514/284

[56] References Cited

U.S. PATENT DOCUMENTS 4,310,667 12/1982 Le Pecq et al. ............ 546/70
4,816,462  3/1989 Nowicky ................. 514/284

OTHER PUBLICATIONS

Proc. Am. Assn for Cancers Res, 73rd meeting, Abstract 593 (1982).
Proc. Am. Assn For Cancer Res. 74th meeting, Absract 656 (1983).
Proc. Am. Assn for Cancer Res. 80th meeting, Abstr. 996(1989).
Auclair et al., Cancer Res., vol. 47, pp. 6254-6261 (1987).
NCI-EORTC Symposium, 1989, Abstracts 435, 436.
Husson, et al., Chem. Abstracts, vol. 97 (1982), entry 6598.
Chemical Abstracts No. 97:6608d; Husson et al.; vol. 97, 1982, p. 638.

Primary Examiner—Donald G. Daus
Attorney, Agent, or Firm—Bacon & Thomas

[57] ABSTRACT

The invention relates to the 2-aminoalkyl-9-hydroxyellipticinium chloride hydrochloride of formula:

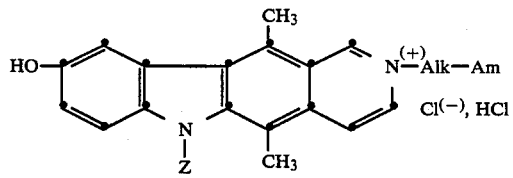

in which Z represents hydrogen or a lower alkyl group, Alk represents a lower alkylene group and Am represents a di(lower alkyl)amino, pyrrolidino or piperidino group.

These compounds are useful as antitumour agents.

9 Claims, No Drawings

HYDROCHLORIDES OF CHLORIDES OF 2-AMINOALKYL-9-HYDROXY-ELLIPTICINIUM DERIVATIVES AND PHARMACEUTICAL COMPOSITIONS CONTAINING THEM

The present invention relates to the hydrochlorides of chlorides of 2-aminoalkyl-9-hydroxyellipticinium derivatives, a process for the preparation thereof and pharmaceutical compositions containing the said compounds as active ingredients.

Water-soluble quaternary salts of 9-hydroxyellipticines of formula:

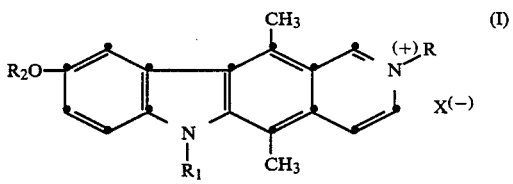

in which $R_1$ is hydrogen or an alkyl group, $R_2$ is hydrogen, an alkyl group or an acyl group, R is an optionally substituted alkyl group and $X^{(-)}$ is an appropriate quaternization anion, have been described in U.S. Pat. No. 4,310,667.

The water-soluble quaternary salts of formula (I) above are prepared by treating the corresponding 9-hydroxyellipticine with the halide $R-X_1$, $X_1$ representing a halogen atom, and by converting the ellipticinium halide thereby obtained, which is virtually insoluble in water, to a corresponding water-soluble salt by means of an ion exchange resin.

In U.S. Pat. No. 4,310,667, mentioned above, all the examples dealing with the intermediate quaternary halides only relate to bromides or iodides.

Among, the water-soluble quaternary salts of the above patent, the acetates are indicated as being preferred; the compound of formula (II) in which $R_1$ and $R_2$ are hydrogen, R represents methyl and $X^{(-)}$ represents the anion acetate is, indeed, used in human therapy for the treatment of tumour forms. This compound, which has received the International Nonproprietary Name "elliptinium acetate" is currently available on the market in the form of a lyophilisate containing a 60.65 mg dose of elliptinium acetate, the lyophilisate being intended to be taken up in 10 ml of water for injectable preparations.

Other compounds which are more active and more hydrosoluble than elliptinium acetate are described in the same U.S. Patent namely compounds of formula (I) above in which $X^{(-)}$ represents the anion acetate, $R_1$ and $R_2$ represent hydrogen and R represents an ethyl group substituted by a diethylamino or piperidino group. However, these 2-aminoalkyl-9-hydroxyellipticinium acetates as well as their preparation present certain disadvantages rendering these compounds of practically no use as ingredients of pharmaceutical compositions.

For instance, the 2-aminoalkyl-9-hydroxyellipticinium acetates in question were found to be much more unstable than elliptinium acetate particularly in solution so that operations of lyophilisation and putting in pharmaceutical form will be extremely difficult in practice. Furthermore, the preparation of the 9-hydroxyellipticinium acetates described in the aforesaid U.S. Patent involves a step which consists in passing on an anion exchange resin.

This method however presents certain inconveniences.

For example, in the preparation of elliptinium acetate as set out in the U.S. Patent in question a step involving momentary transformation to a metastable solution of an ellipticinium derivative is described.

This solution must be used very rapidly in the subsequent operations. Moreover, this method for obtaining acetate derivatives frequently gives rise to by-products which are particularly undesirable when subsequent operations of preparation of pharmaceutical compositions are to be undertaken.

The acetate formed subsequently to the anion exchange operation and more particularly the acetate of the 2-aminoalkyl-9-hydroxyellipticinium derivatives, for instance 2-(2-diethylaminoethyl)-9-hydroxyellipticinium acetate, was found to be contaminated with impurities such as polymers or oligomers. These impurities must be eliminated necessitating an additional step of purification which leads to a loss of yield in the desired product.

It has now been found, surprisingly, that the hydrochlorides of chlorides of 2-aminoalkyl-9-hydroxyellipticinium derivatives possess several advantages relative to the previous acetate derivatives and, in particular, relative to elliptinium acetate.

Thus, with the hydrochlorides of chlorides of 2-aminoalkyl-9-hydroxyellipticinium derivatives, it has been possible to demonstrate very great solubility in water as well as very good stability both in the solid state and in solution. For example, the solubility in water of 2-(2-diethylaminoethyl)-9-hydroxyellipticinium chloride hydrochloride is at least 50 mg/ml.

Furthermore, the preparation of pharmaceutical compositions containing the hydrochlorides of chlorides of 2-aminoalkyl-9-hydroxyellipticinium derivatives in question and more particularly 2-(2-diethylaminoethyl)-9-hydroxyellipticinium chloride hydrochloride can be very easily carried out.

In consequence, for the preparation of the active principle intended to be incorporated in proprietary medicinal products, 100 mg of 2-(2-diethylaminoethyl)-9-hydroxyellipticinium chloride hydrochloride can be dissolved in 2 ml of water for the purpose of lyophilization, and 100 mg of the lyophilisate thereby obtained can then be dissolved in 5 or 10 ml of water for injectable preparations.

In contrast, in the case of elliptinium acetate, 60 mg of this salt can be dissolved in 4 ml of water for the lyophilization operation. However, the upper limit of solubility of the product is only 60 mg of lyophilisate in 10 ml of water. At higher concentrations, the rate of dissolution of elliptinium acetate in water is in fact too slow, when the clinical requirements are taken into account.

It is hence possible to prepare solutions of hydrochlorides of chlorides of 2-aminoalkyl-9-hydroxyellipticinium and more particularly solutions of 2-(2-diethylaminoethyl)-9-hydroxyellipticinium chloride hydrochloride at a concentration higher than that of elliptinium acetate, and this, associated with a lower toxicity of the product, enables the programming of the patient's treatment to be improved.

Furthermore, relative to the products of U.S. Pat. No. 4,310,667, the chloride hydrochloride have the advantage of not involving anion exchange in their preparation, but only a simple salification with hydrochloric acid and this results, at the industrial level, in a simplification of the process, and from the standpoint of purity, in an absence of undesirable by-products.

It has also been found that the said hydrochlorides of chlorides of 2-aminoalkyl-9-hydroxyellipticinium derivatives are more active than elliptinium acetate and, at least as active as the corresponding compound bearing the acetate anion.

Finally, it has been found that the said hydrochlorides of chlorides of 2-aminoalkyl-9-hydroxyellipticinium derivatives are less toxic and have fewer side effects than elliptinium acetate.

Thus, according to one of its aspects, the present invention relates to the hydrochloride of the chloride of a 2-aminoalkylellipticinium derivative, represented by the following formula:

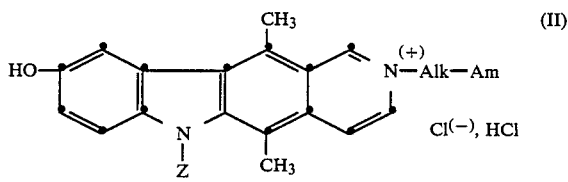
(II)

in which Z represents hydrogen or a lower alkyl group, Alk represents a lower alkylene group and Am represents a di(lower alkyl)amino, pyrrolidino or piperidino group.

The "lower alkyl" group, as used in the present description and in the claims, represents the monovalent radical of a saturated aliphatic hydrocarbon containing up to 4 carbon atoms, such as methyl, ethyl, propyl, isopropyl or n-butyl.

The "lower alkylene" group, as used in the present description and in the claims, represents the non-geminal divalent radical of a saturated aliphatic hydrocarbon containing from 2 to 4 carbon atoms, such as 1,2-ethylene, 1,2-propylene, 1,3-propylene or 1,4-butylene.

The di(lower alkyl)amino group represented by Am can be symmetrical as in the case of a dimethylamino, diethylamino or diisopropylamino radical, or assymetrical, as in the case of a methylethylamino, methylpropylamino or ethylpropylamino radical.

The 2-aminoalkylellipticinium derivatives of formula (II) in which -Alk-Am represents a diethylaminoethyl or piperidinoethyl radical constitute a preferred class of compounds of the invention.

Furthermore, 2-(2-piperidinoethyl)-9-hydroxyellipticinium chloride hydrochloride and more particularly 2-(2-diethylaminoethyl)-9-hydroxyellipticinium chloride hydrochloride can be regarded as preferred compounds of the invention.

According to another of its aspects, the present invention relates to a process for preparing the compounds of formula (II) above, whereby a 9-hydroxyellipticine of formula:

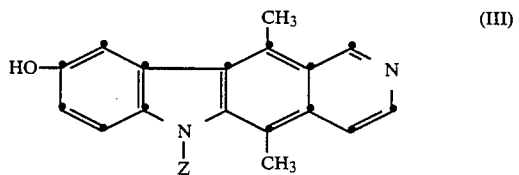
(III)

in which Z is as defined above, is treated with a chloroalkylamine of general formula:

Cl—Alk—Am (IV)

in which Alk and Am are as defined above, in an inert organic solvent at a temperature between room-temperature and 140° C., and the quaternary chloride thereby obtained, of formula:

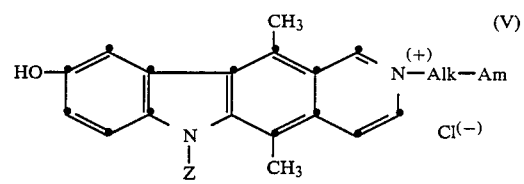
(V)

in which Z, Alk and Am are as defined above, is then converted to its hydrochloride by treatment with hydrochloric acid.

The reaction of the compounds (III) with the compounds (IV) is performed according to the methods known in the literature for preparing quaternary ammonium compounds.

The solvent used is preferably a polar aprotic solvent such as dimethylformamide, dimethylacetamide or dimethylsulphoxide, but other solvents which are inert under the reaction conditions can be used.

The reaction time depends on the temperature; in general, at a temperature of 90° to 130° C., the reaction is complete after 2-4 hours of heating, and the product (V) thereby obtained is isolated according to conventional procedures, for example by precipitation with a suitable solvent such as diethyl ether.

The compounds of formula (V) above are new.

The conversion of the compounds (V) to the hydrochlorides of the present invention is performed according to the well known methods of salification.

The salification of the compound (V) is preferably performed with an aqueous alcoholic solution of hydrochloric acid and the hydrochloride is isolated according to the usual techniques.

The compounds of formula (II) above were found to be much more active and less toxic than elliptinium acetate and their antitumour activity was found to be at least equal to that of the corresponding acetates in all the tests of antitumour activity performed.

For instance, the antitumoral activity of the compounds of the invention was tested in respect of leukemia L 1210 in the mouse.

To this end, CDF1 strain male mice were divided in groups of 10 animals and a tumoral inoculum of $1.10^5$ L 1210 leukemia cells of LEA 03B06 strain in 0.1 ml of distilled water was administered by intraperitoneal route to each mouse.

After 24 h, a single dose of the compound to be studied was administered by intraperitoneal route to half of the groups of mice and the same volume of solvent to the other half of the groups, this latter half representing the control groups. On the 60th day after inoculation, the number of surviving animals was noted and the activity was measured by determining the increase in survival time of the treated animals in comparison with the controls. This activity was expressed as follows:

$$\frac{T}{C} = \frac{\text{mean survival of treated animals}}{\text{mean survival of control animals}} \times 100$$

the mean survival of the treated animals taking into account the surviving animals.

In this test, the compound of Example 1 (SR 95156 B) showed some activity at 10 mg/kg (1/10 surviving animal on the 60th day) and good activity at 20 mg/kg (3/10 survivors) and at 50 mg/kg (5/10 survivors).

Another representative compound of the present invention SR 95157 B (Example 2) was found to be active at 20 mg/kg (2/10 survivors) and at 50 mg/kg (5/10 survivors).

At 50 mg/kg, the relative survival T/C of SR 95156 B was 375% and 386% for SR 95157 B.

In the same test, no control animal or animals treated with 50 mg/kg of elliptinium acetate or 200 mg/kg of 5-fluoro-uracile survived.

Administered at the dose of 10 mg/kg elliptinium acetate induced a relative survival T/C of 154% with no survivors.

A further trial performed with SR 95156 B in the form of a pharmaceutical composition (100 mg of lyophilisate dissolved in 10 ml of water for injection) confirmed the above results.

At the dose of 50 mg/kg the relative survival T/C was 439% with 5 surviving mice.

Furthermore, in toxicity tests, it was possible to demonstrate a lower acute toxicity and a lower nephrotoxicity of the chloride hydrochlorides of the invention relative to the corresponding chloride.

Thus, by intraperitoneal route in mice 2-(2-diethylaminoethyl)-9-hydroxyellipticinium chloride hydrochloride (SR 95156 B) has shown an acute toxicity $LD_{50}$ of 75 mg/kg while, in the same conditions elliptinium acetate has revealed a $LD_{50}$ of 10.2 mg/kg [Recent Results in Cancer Research, 74, pp. 107–123 (1980)].

Similarly, the Table below which reports the results obtained in nephrotoxicity tests carried out with 2-(2-diethylaminoethyl)-9-hydroxyellipticinium chloride hydrochloride (SR 95156 B) in comparison with an acetate derivative, in this case elliptinium acetate, shows the superiority of the compound of the invention over the known compound.

TABLE

Comparative nephrotoxicity in rats after repetitive injection of the compound being studied.

| Dose (5 mg/kg) | Kidney weight as relative value (g/100) | Urea (mM) | Creatinine $\mu M$ | Histopathology (proximal tubulopathy) |
|---|---|---|---|---|
| Elliptinium acetate | 0.87 | 6.5 | 91.2 | +++ |
| SR 95156 B | 0.70 | 3.8 | 60.4 | about + |
| Controls | 0.68 | 3.2 | 55.2 | none |

+++: considerable
++: moderate
+: low

The compounds of the invention can be used for the treatment of tumour forms which are sensitive to ellipticine derivatives.

The invention also relates to a method for treating tumor forms which are sensitive to ellipticine derivatives comprising the administration to the subject in need of such treatment of an effective dose of at least one chloride hydrochloride of the invention.

For this purpose, doses of 50 to 500 mg/m$^2$, for example, will be used per course of treatment, in general per repeated 3-day treatment.

Thus, according to another of its aspects, the present invention relates to pharmaceutical compositions comprising at least one compound of formula (II) above as an active ingredient.

The pharmaceutical compositions of the invention can be present in appropriate forms suitable for administration in human or veterinary therapy, preferably in the form of an administration unit for parenteral administration.

The total amount of active principle can vary from 50 to 500 mg per administration unit, the said active principle preferably being associated with pharmaceutical vehicles, in particular distilled water.

In general, compositions according to the invention are prepared by dissolving the active principle according to the invention in water, lyophilizing the solution and introducing the lyophilisate obtained into water for injections or physiological saline. The solution thereby obtained can be introduced into bottles for intravenous perfusion containing, for example, glucose solution.

The preferred administration form will consist of a bottle of 50 to 500 mg of active principle according to the invention, which is intended to be dissolved in 5 to 20 ml of water for injections or physiological saline contained in an ampoule.

The non-limitative Examples which follow illustrate the invention.

EXAMPLE 1

2-(2-Diethylaminoethyl)-9-hydroxyellipticinium chloride hydrochloride (a) 2-(2-Diethylaminoethyl)-9-hydroxyellipticinium chloride A solution of 9-hydroxyellipticine (obtained by neutralization of 23.3 mmols of its hydrobromide) in 100 ml of dimethylformamide was heated to 100° C. A solution of 1-chloro-2-diethylaminoethane (obtained by neutralization of 58 mmols of its hydrochloride) in 20 ml of diethyl ether was then added gradually and with stirring while the ether was distilled off as it was introduced. After 3 hours at 100° C. with stirring, the reaction products began to precipitate. After the mixture was cooled, the precipitate was filtered off. It was washed with 10 ml of dimethylformamide and then with twice 25 ml of diethyl ether, and was then dried at 40° C. under reduced pressure.

In this manner, 6.9 g of orange-coloured crude 2-(2-diethylaminoethyl)-9-hydroxyellipticinium chloride were isolated.

(b) 2-(2-Diethylaminoethyl)-9-hydroxyellipticinium chloride hydrochloride

In a solution consisting of 2.45 ml of 12N hydrochloric acid, 26 ml of water and 180 ml of ethanol were dissolved 6.9 g of 2-(2-diethylaminoethyl)-9-hydroxyellipticinium chloride, the solution being brought beforehand to reflux.

After this operation, 0.25 g of activated charcoal was added and the solution was filtered hot. After the mixture was cooled, the precipitate was filtered off and washed with 20 ml of absolute ethanol and then with twice 30 ml of acetone. It was then dried at 50° C. for 12 hours.

In this manner, 5.64 g of brick-red pure 2-(2-diethylaminoethyl)-9-hydroxyellipticinium chloride hydrochloride (SR 95156 B) were obtained. Purity by HPLC (high pressure liquid chromatography): 99.8%. The IR (infrared) and H NMR (proton nuclear magnetic resonance) spectra confirmed the structure of the product. The overall yield was 56% with respect to the 9-hydroxyellipticine hydrobromide.

EXAMPLE 2

2-(2-Piperidinoethyl)-9-hydroxyellipticinium chloride hydrochloride

Using the procedure described in Example 1(a), a solution of 9-hydroxyellipticine (obtained by neutralization of 44 mmols of its hydrobromide) in 480 ml of dimethylformamide was treated at 110°–130° C. for 5 hours with a solution of 1-chloro-2-piperidinoethane (obtained by neutralization of 110 mmols of its hydrochloride). A portion (15 g) of the orange-coloured 2-(2-piperidinoethyl)-9-hydroxyellipticinium chloride thereby obtained was then salified with a solution of 5.1 ml of 12N-hydrochloric acid, 260 ml of water and 240 ml of ethanol, as described in Example 1(b).

In this manner, 12.3 g of orange-coloured pure 2-(2-piperidinoethyl)-9-hydroxyellipticinium chloride hydrochloride (SR 95157 B) were obtained.

Elementary analysis (referred to the dehydrated products):

| Calculated | C %: 64.57 | H %: 6.55 | N %: 9.41 |
|---|---|---|---|
| Found | 64.68 | 6.55 | 9.71 |

Chlorides: 16.56%
HPLC purity: 99.4%

The IR and H NMR spectra confirmed the structure of the product. The overall yield was 84% with respect to the 9-hydroxyellipticine hydrobromide.

EXAMPLE 3

2-(2-Diethylaminoethyl)-9-hydroxyellipticinium chloride hydrochloride

The procedure described in Example 1 was repeated exactly, starting with 9-hydroxyellipticine obtained by neutralization of 300 g of its hydrobromide. The final product obtained was identical to SR 95156 B of Example 1. Overall yield with respect to the 9-hydroxyellipticine hydrobromide: 68%.

EXAMPLES 4 TO 9

Using the procedure described in Example 1, by treatment of 9-hydroxyellipticine with 1-chloro-2-diisopropylethane, 1-chloro-2-(ethylmethylamino)-ethane and 1-chloro-2-pyrrolidinoethane respectively, the following compounds were obtained:

2-(2-diisopropylaminoethyl)-9-hydroxyellipticinium chloride hydrochloride (Ex. 4);
2-[2-(ethylmethylamino)ethyl]-9-hydroxyellipticinium chloride hydrochloride (Ex. 5); and
2-(2-pyrrolidinoethyl)-9-hydroxyellipticinium chloride hydrochloride (Ex. 6).

With 9-hydroxyellipticine replaced by 6-methyl-9-hydroxyellipticine, the same procedure being used, the following compounds were obtained:

2-(2-diisopropylaminoethyl)-6-methyl-9-hydroxyellipticinium chloride hydrochloride (Ex. 7);
2-[2-(ethylmethylamino)ethyl]-6-methyl-9-hydroxyellipticinium chloride hydrochloride (Ex. 8); and
2-(2-pyrrolidinoethyl)-6-methyl-9-hydroxyellipticinium chloride hydrochloride (Ex. 9).

EXAMPLES 10 TO 13

By reacting 1-chloro-2-diethylaminoethane with 6-methyl-9-hydroxyellipticine and 6-ethyl-9-hydroxyellipticine respectively, as described in Example 1, the following compounds were obtained:

2-(2-diethylaminoethyl)-6-methyl-9-hydroxyellipticinium chloride hydrochloride (Ex. 10); and
2-(2-diethylaminoethyl)-6-ethyl-9-hydroxyellipticinium chloride hydrochloride (Ex. 11).

With 1-chloro-2-diethylaminoethane replaced by 1-chloro-2-piperidinoethane, and the same procedure being used, the following compounds were obtained:

2-(2-piperidinoethyl)-6-methyl-9-hydroxyellipticinium chloride hydrochloride (Ex. 12); and
2-(2-piperidinoethyl)-6-ethyl-9-hydroxyellipticinium chloride hydrochloride (Ex. 13).

EXAMPLE 14

An injectable pharmaceutical composition was prepared by dissolving 100 mg of the compound of Example 1 or Example 2 in 2 ml of water, lyophilizing the solution obtained and redissolving the lyophilisate in 10 ml of water for injections.

We claim:

1. 2-Aminoalkyl-9-hydroxyellipticinium chloride hydrochloride of formula:

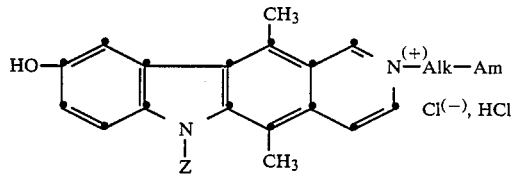

in which Z represents hydrogen or a lower alkyl group, Alk represents a lower alkylene group and Am represents a di(lower alkyl) amino, pyrrolidino or piperidino group.

2. 2-Aminoalkyl-9-hydroxyellipticinium chloride hydrochloride according to claim 1 in which Alk represents an ethylene group and Am represents a diethylamino or piperidino group.

3. 2-(2-Diethylaminoethyl)-9-hydroxyellipticinium chloride hydrochloride.

4. 2-(2-Piperidinoethyl)-9-hydroxyellipticinium chloride hydrochloride.

5. A pharmaceutical composition having antitumor activity comprising an effective amount of a compound as claimed in claim 1 in admixture with a pharmaceutically acceptable excipient.

6. A pharmaceutical composition having antitumor activity comprising an effective amount of a compound as claimed in claim 3 in admixture with a pharmaceutically acceptable excipient.

7. A pharmaceutical composition having antitumor activity comprising an effective amount of a compound as claimed in claim 4 in admixture with a pharmaceutically acceptable excipient.

8. A pharmaceutical composition according to claim 5 in the form of an administration unit for parenteral administration.

9. A pharmaceutical composition having anti leukemia activity comprising an effective amount of a compound as claimed in claim 1 in admixture with a pharmaceutically acceptable excipient.

* * * * *